(12) United States Patent
Prazak

(10) Patent No.: US 6,258,074 B1
(45) Date of Patent: Jul. 10, 2001

(54) INTERLABIAL ABSORBENT DEVICE

(76) Inventor: Lisa K. Prazak, 2317 S. Old Bastrop Hwy., San Marcos, TX (US) 78666

( * ) Notice: Subject to any disclaimer, the term of this patent is extended or adjusted under 35 U.S.C. 154(b) by 0 days.

(21) Appl. No.: 09/405,708

(22) Filed: Sep. 24, 1999

(51) Int. Cl.$^7$ .............................. A61F 13/15; A61F 13/20
(52) U.S. Cl. .............. 604/385.17; 604/358; 604/385.01; 604/385.04; 604/385.03
(58) Field of Search .................. 604/385.04, 385.17, 604/385.101, 385.28, 387, 385.01

(56) References Cited

U.S. PATENT DOCUMENTS

| | | | |
|---|---|---|---|
| 4,595,392 | * 6/1986 | Johnson et al. ...................... | 604/385 |
| 5,489,283 | * 2/1996 | Tillburg ................................ | 604/387 |
| 5,542,941 | * 8/1996 | Morita ................................ | 604/385.1 |
| 5,873,869 | * 2/1999 | Hammons et al. ................ | 604/385.1 |
| 5,916,205 | * 6/1999 | Olson et al. ....................... | 604/385.1 |
| 5,964,689 | * 10/1999 | McFall et al. ...................... | 493/395 |

* cited by examiner

Primary Examiner—Aaron J. Lewis
Assistant Examiner—Michele Kidwell

(57) ABSTRACT

A feminine sanitary pad for providing an absorbent barrier to menses and other vaginal discharges. The feminine sanitary pad includes a pad having a central portion and a pair of side wings each extending between the ends of the pad. Each of the side wings is bendable with respect to the central portion along corresponding unions between the central portion and the respective side wing.

8 Claims, 2 Drawing Sheets

INTERLABIAL ABSORBENT DEVICE

BACKGROUND OF THE INVENTION

1. Field of the Invention

The present invention relates to absorbent feminine sanitary articles and more particularly pertains to a new feminine sanitary pad for providing an absorbent barrier to menses and other vaginal discharges.

2. Description of the Prior Art

The use of absorbent feminine sanitary articles is known in the prior art. More specifically, absorbent feminine sanitary articles heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,098,422; 3,906,952; 5,542,941; 4,631,062; 5,484,429; and U.S. Pat. No. Des. 249,280.

While these devices fulfill their respective, particular objectives and requirements, the aforementioned patents do not disclose a new feminine sanitary pad. The inventive device includes a pad having a central portion and a pair of side wings each extending between the ends of the pad. Each of the side wings is bendable with respect to the central portion along corresponding unions between the central portion and the respective side wing.

In these respects, the feminine sanitary pad according to the present invention substantially departs from the conventional concepts and designs of the prior art, and in so doing provides an apparatus primarily developed for the purpose of providing an absorbent barrier to menses and other vaginal discharges.

SUMMARY OF THE INVENTION

In view of the foregoing disadvantages inherent in the known types of absorbent feminine sanitary articles now present in the prior art, the present invention provides a new feminine sanitary pad construction wherein the same can be utilized for providing an absorbent barrier to menses and other vaginal discharges.

The general purpose of the present invention, which will be described subsequently in greater detail, is to provide a new feminine sanitary pad apparatus and method which has many of the advantages of the absorbent feminine sanitary articles mentioned heretofore and many novel features that result in a new feminine sanitary pad which is not anticipated, rendered obvious, suggested, or even implied by any of the prior art absorbent feminine sanitary articles, either alone or in any combination thereof.

To attain this, the present invention generally comprises a pad having a central portion and a pair of side wings each extending between the ends of the pad. Each of the side wings is bendable with respect to the central portion along corresponding unions between the central portion and the respective side wing.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new feminine sanitary pad apparatus and method which has many of the advantages of the absorbent feminine sanitary articles mentioned heretofore and many novel features that result in a new feminine sanitary pad which is not anticipated, rendered obvious, suggested, or even implied by any of the prior art absorbent feminine sanitary articles, either alone or in any combination thereof.

It is another object of the present invention to provide a new feminine sanitary pad which may be easily and efficiently manufactured and marketed.

It is a further object of the present invention to provide a new feminine sanitary pad which is of a durable and reliable construction.

An even further object of the present invention is to provide a new feminine sanitary pad which is susceptible of a low cost of manufacture with regard to both materials and labor, and which accordingly is then susceptible of low prices of sale to the consuming public, thereby making such feminine sanitary pad economically available to the buying public.

Still yet another object of the present invention is to provide a new feminine sanitary pad which provides in the apparatuses and methods of the prior art some of the advantages thereof, while simultaneously overcoming some of the disadvantages normally associated therewith.

Still another object of the present invention is to provide a new feminine sanitary pad for providing an absorbent barrier to menses and other vaginal discharges.

Yet another object of the present invention is to provide a new feminine sanitary pad which includes a pad having a central portion and a pair of side wings each extending between the ends of the pad. Each of the side wings is bendable with respect to the central portion along corresponding unions between the central portion and the respective side wing.

Still yet another object of the present invention is to provide a new feminine sanitary pad that is more absorbent than most commercial tampons and feminine hygiene pads to provide sufficient absorbing protection from heavy menstrual flows.

Even still another object of the present invention is to provide a new feminine sanitary pad that may be worn discretely under tight fitting clothes.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
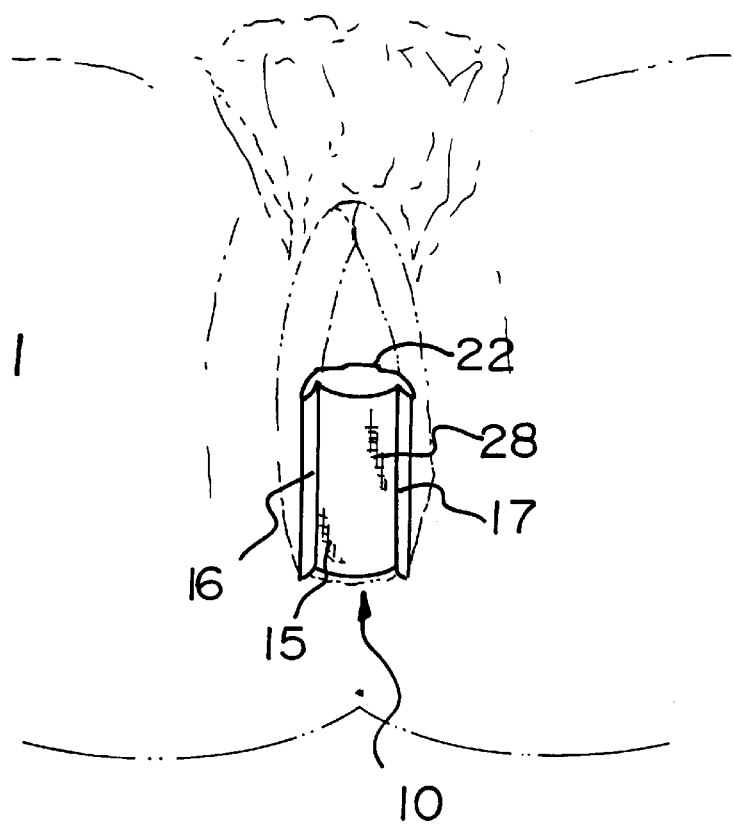
FIG. 1 is a schematic perspective view of a new feminine sanitary pad in use inserted into a female user's vagina according to the present invention.

With reference now to the drawings, and in particular to FIGS. 1 through 4 thereof, a new feminine sanitary pad embodying the principles and concepts of the present invention will be described.

As best illustrated in FIGS. 1 through 4, the feminine sanitary pad generally comprises a pad having a central portion and a pair of side wings each extending between the ends of the pad. Each of the side wings is bendable with respect to the central portion along corresponding unions between the central portion and the respective side wing.

In closer detail, the sanitary pad comprises a pad 10 having a pair of opposite ends 11,12, and a pair of sides 13,14 extending between the ends of the pad. The ends of the pad lie in generally parallel planes to one another and the sides of the pad are extended generally parallel to one another and generally perpendicular to the ends of the pad. The pad has a length defined between the ends of the pad and a width defined between the sides of the pad. Preferably, the length and width of the pad are each at least about 1 inch. Ideally, the length of the pad is between about 2 inches and about 4 inches, and the width of the pad is about 3 inches.

The pad comprises a central portion 15 and a pair of side wings 16,17 each extending between the ends of the pad. One of the side wings is located at one side of the pad and the other of the side wings is located at the other of the sides of the pad so that the central portion is interposed between the side wings. In use, each of the side wings is bendable with respect to the central portion along corresponding unions 18,19 between the central portion and the respective side wing. Each union is extended generally parallel to the sides of the pad and generally perpendicular to the ends of the pad.

Figure 2:
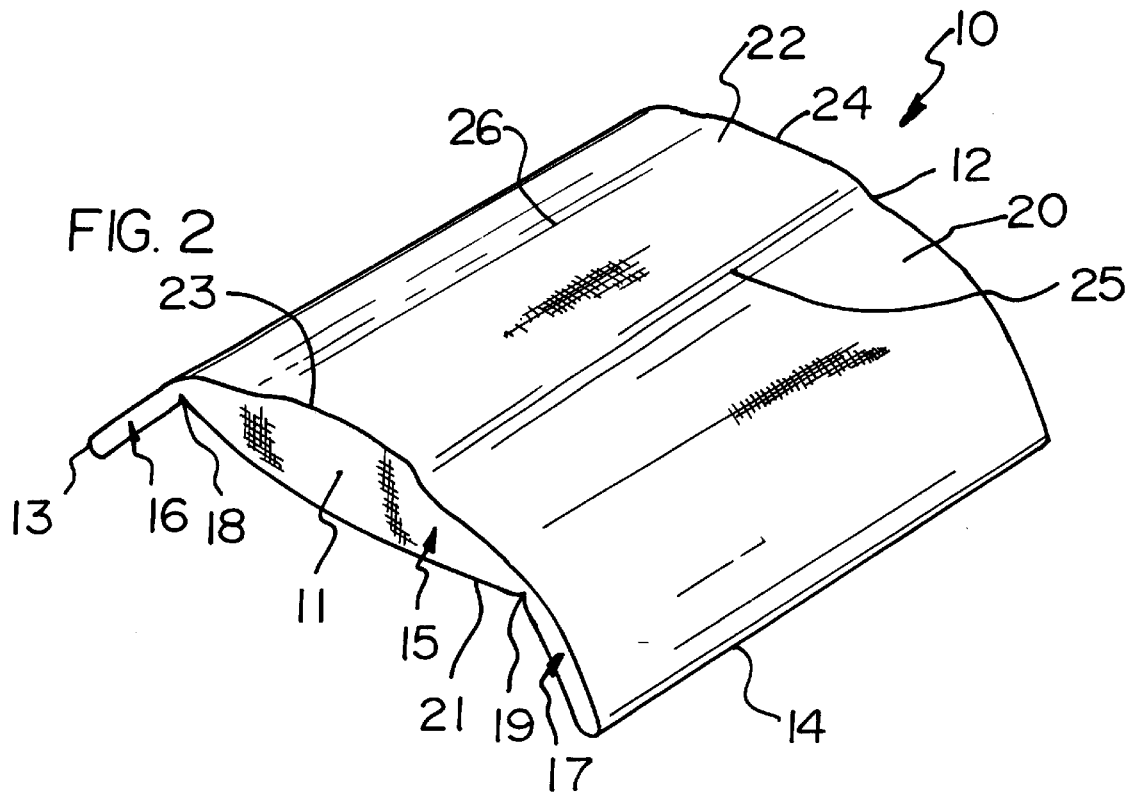
FIG. 2 is a schematic perspective view of the present invention.

The side wings and the central portion have continuous upper faces 20 and continuous lower faces 21. As best illustrated in FIG. 2, the upper face of each side wing is extended generally parallel to the lower face of the respective side wing. The upper and lower faces of the central portion each are curved or arcuate and has concavities facing one another so that upper and lower faces of the central portion each have an outwardly facing convexity. The upper and lower faces of the central portion each have a radius of curvature lie in a plane generally parallel to the ends of the pad with each radius of curvature defining a continuous corresponding arc extending substantially across the respective face of the central portion between the unions between the central portion and the side wings. The radius of curvature of the upper face of the central portion is greater than the radius of curvature of the lower face of the central portion such that the lower face of the central portion has a sharper curve than the upper face of the central portion.

The upper face of the central portion also preferably has an elongate center ridge 22 extending between the ends of the pad preferably generally equidistantly positioned between the unions between the side wings and the central portion. The center ridge has a generally rectangular outer perimeter comprising a pair of ends 23,24 extending generally parallel to the ends of the pad and a pair of sides 25,26 extending generally parallel to the sides of the pad. Preferably, each end of the center ridge is generally coplanar with an associated adjacent end of the pad.

The central portion has a width defined between the unions, the center ridge has a width defined between the sides of the outer perimeter of the center ridge. Preferably, the width of the center ridge is between about one-fifth and about four-fifths the width of the central region. Ideally, the width of the center ridge is about one-half the width of the central portion.

The side wings each preferably have a generally uniform thickness defined between the upper and lower faces of the respective side wing. The central portion has a maximum thickness defined between the center ridge and a nadir of the lower face of the central portion located on the lower face of the central portion opposite the center ridge of the central portion. Preferably, the thickness' of the side wings are about equal to one another. In this preferred embodiment, the maximum thickness of the central portion is at least about twice the thickness of either side wing. Ideally, the maximum thickness of the central portion is about three times the thickness of either side wing. In an ideal illustrative embodiment, the thickness of each side wing is about ½ inch and the maximum thickness of the central portion is about 1½ inches.

Figure 3:
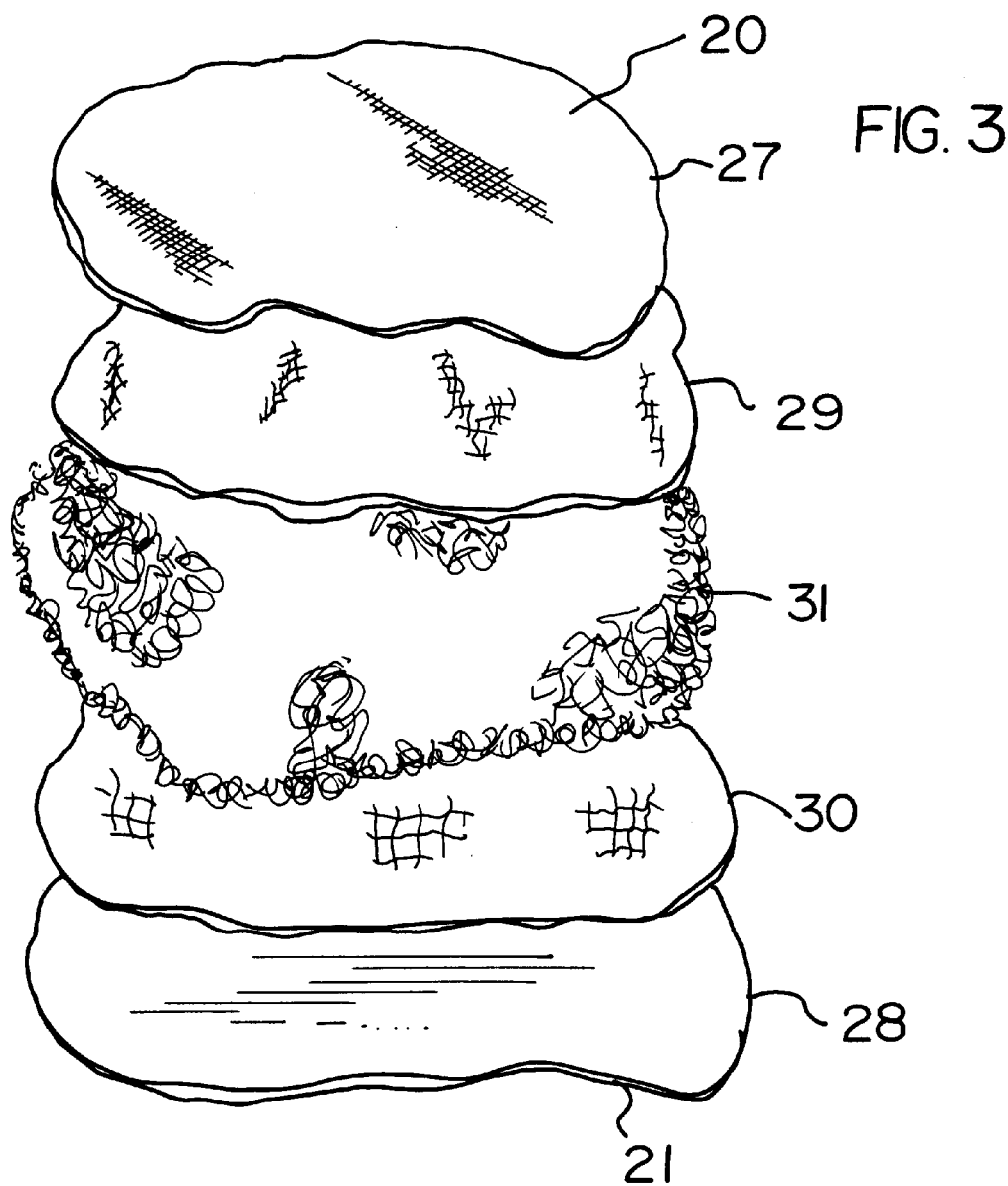
FIG. 3 is a schematic enlarged exploded perspective view of the layers of the present invention.

With reference to FIG. 3, the pad comprises a plurality of generally coextensive layers that are preferably all biodegradable so that the pad may be safely disposed of by flushing down a toilet. The plurality of layers includes a flexible water permeable woven fabric material upper layer 27 defining the upper faces of the side wings and central portion of the pad, a substantially water-impermeable flexible plastic material lower layer 28 defining the lower faces of the side wings and the central portion of the pad, a pair of flexible water permeable woven fabric material inner layers 29,30 interposed between the upper and lower layers, and a water-absorbent cotton packing middle layer 31 interposed between the inner layers. Preferably, the inner layers each have a looser, more open weave than said upper layer.

The middle layer has a thickness defined between the inner layers. The thickness of the middle layer located in the central portion of the pad is at least about one-half the maximum thickness of the central portion so that the maximum capacity for absorption of the middle layer is located in the central portion with lesser capacity in the side wings.

Figure 4:
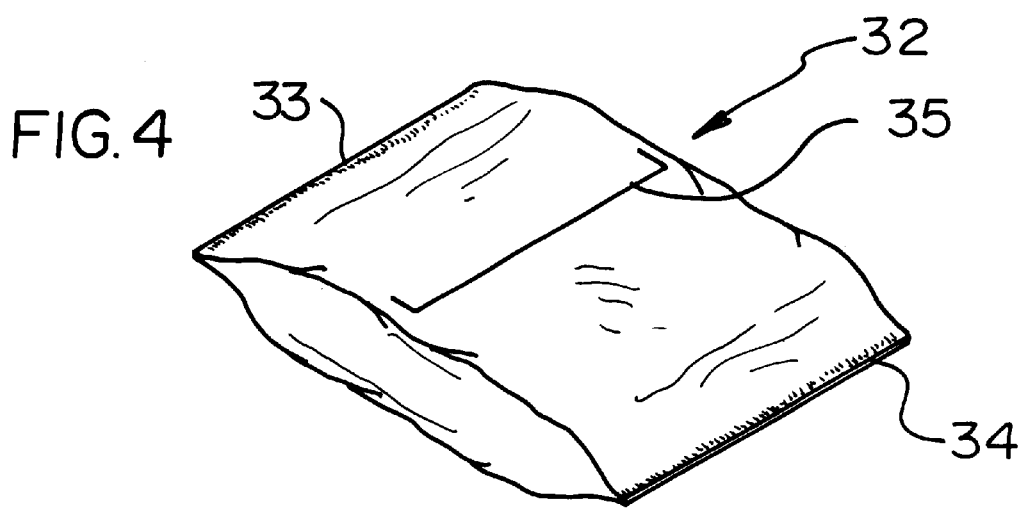
FIG. 4 is a schematic perspective view of a package enclosing the present invention.

Preferably, the pad is enclosed in a package 32 as illustrated in FIG. 4. The package has a pair of side seams 33,34. One of the side seams is located adjacent one of the sides of the and the other of the side seams is located adjacent the other side of the pad. The package also has a top flap 35 extending therefrom located adjacent the central portion of the pad. In use, the top flap is designed for aiding the tearing of the package to provide access to the pad.

The sanitary pad is designed for insertion into a female user's vagina for absorbing menses and other menstrual fluids. In use, a user first positions the central portion of the pad adjacent the user's vagina with the upper face of the central portion facing into the user's vagina, the ends of the pad face in forwards and rearwards directions with respect to the user so that each side wing is positioned adjacent an corresponding leg of the user. The user then places a finger such as the index finger on the lower face of the central portion and presses the central portion into the user's vagina with the finger, as the central portion is pressed into the vagina, the side wings are bent down along the unions so that a portion of each side wing downwardly extends from the user's vagina, as illustrated in FIG. 1, to provide additional absorbing protection to the sides of the user's vagina to absorb menstrual fluids that escape absorption in the central portion. To remove the pad, the user simply grasps the side wings and pulls the pad out of the user's vagina.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An absorbent feminine hygiene article for insertion into a female user's vagina, said absorbent feminine hygiene article comprising:
    a pad having a pair of opposite ends, and a pair of sides extending between said ends of said pad;
    said pad comprising a central portion and a pair of side wings each extending between said ends of said pad;
    each of said side wings being bendable with respect to said central portion along corresponding unions between said central portion and the respective side wing, and
    wherein an upper face of said central portion has an elongate center ridge extending between said ends of said pad, said center ridge having a width less than a width of said central portion such that said center ridge is adapted for insertion into a labium minora of the female user and the central portion is adapted for abutting against the labium minora of the female user for preventing fluid bypassing said central portion.

2. The absorbent feminine hygiene article of claim 1, wherein said side wings and said central portion have continuous upper faces and continuous lower faces, said upper face of each side wing is extended generally parallel to said lower face of the respective side wing, and said upper and lower faces of said central portion each is curved and has concavities facing one another such that upper and lower faces of said central portion each have an outwardly facing convexity.

3. The absorbent feminine hygiene article of claim 2, wherein said upper and lower faces of said central portion each have a radius of curvature lying in a plane generally parallel to said ends of said pad with each radius of curvature defining a continuous corresponding arc such that said central portion has an arcuate cross section substantially across the respective face of said central portion.

4. The absorbent feminine hygiene article of claim 3, wherein said radius of curvature of said upper face of said central portion is greater than said radius of curvature of said lower face of said central portion.

5. The absorbent feminine hygiene article of claim 1, wherein said pad comprises a plurality of generally coextensive layers, said plurality of layers including a flexible water permeable woven fabric material upper layer defining said upper faces of said side wings and central portion of said pad, a substantially water-impermeable flexible plastic material lower layer defining said lower faces of said side wings and said central portion of said pad, a pair of flexible water permeable woven fabric material inner layers interposed between said upper and lower layers, and a water-absorbent cotton packing middle layer interposed between said inner layers.

6. An absorbent feminine hygiene article for insertion into a female user's vagina, said absorbent feminine hygiene article comprising:
    a pad having a pair of opposite ends, and a pair of sides extending between said ends of said pad;
    said ends of said pad lying in generally parallel planes to one another, said sides of said pad being extended generally parallel to one another and generally perpendicular to said ends of said pad;
    said pad comprising a central portion and a pair of side wings each extending between said ends of said pad, one of said side wings being located at one side of said pad and the other of said side wings being located at the other of said sides of said pad, said central portion being interposed between said side wings;
    each of said side wings being bendable with respect to said central portion along corresponding unions between said central portion and the respective side wing, each union being extended generally parallel to said sides of said pad and generally perpendicular to said ends of said pad;
    said side wings and said central portion having continuous upper faces and continuous lower faces;
    said upper face of each side wing being extended generally parallel to said lower face of the respective side wing;
    said upper and lower faces of said central portion each being curved and having concavities facing one another such that upper and lower faces of said central portion each have an outwardly facing convexity, said upper and lower faces of said central portion each having a radius of curvature lying in a plane generally parallel to said ends of said pad with each radius of curvature defining a continuous corresponding arc extending substantially across the respective face of said central portion between said unions between said central portion and said side wings;

said radius of curvature of said upper face of said central portion being greater than said radius of curvature of said lower face of said central portion such that said lower face of said central portion has a sharper curve than said upper face of said central portion;

upper face of said central portion having an elongate center ridge extending between said ends of said pad generally equidistantly positioned between said unions between said side wings and said central portion;

said center ridge having a generally rectangular outer perimeter comprising a pair of ends extending generally parallel to said ends of said pad and a pair of sides extending generally parallel to said sides of said pad, each end of said center ridge being generally coplanar with an associated adjacent end of said pad;

said central portion having a width defined between said unions, said center ridge having a width defined between said sides of said outer perimeter of said center ridge;

wherein said width of said center ridge is about one-half said width of said central portion such that said center ridge is adapted for insertion into a labium minora of the female user and the central portion is adapted for abutting against the labium minora of the female user for preventing fluid bypassing said central portion;

said side wings each having a generally uniform thickness defined between said upper and lower faces of the respective side wing;

said central portion having a maximum thickness defined between said center ridge and a nadir of said lower face of said central portion located on said lower face of said central portion opposite said center ridge of said central portion;

wherein said thickness' of said side wings are about equal to one another, wherein said maximum thickness of said central portion is at least about twice said thickness of either side wing;

said pad comprising a plurality of generally coextensive layers, said plurality of layers including a flexible water permeable woven fabric material upper layer defining said upper faces of said side wings and central portion of said pad, a substantially water-impermeable flexible plastic material lower layer defining said lower faces of said side wings and said central portion of said pad, a pair of flexible water permeable woven fabric material inner layers interposed between said upper and lower layers, and a water-absorbent cotton packing middle layer interposed between said inner layers;

said middle layer having a thickness defined between said inner layers, said thickness of said middle layer located in said central portion of said pad being at least about one-half said maximum thickness of said central portion such that the maximum capacity for absorption of said middle layer is located in said central portion with lesser capacity in said side wings; and a package substantially enclosing said pad therein, said package having a pair of side seams, one of said side seams being located adjacent one of said sides of said pad and the other of said side seams being located adjacent the other side of said pad, said package having a top flap extending therefrom located adjacent said central portion of said pad, said top flap being adapted for aiding the tearing of said package to provide access to said pad.

7. The absorbent feminine hygiene article of claim 1, wherein said width of said center ridge is about one-half said width of said central portion such that said center ridge is adapted for insertion into a labium minora of the female user and the central portion is adapted for abutting against the labium minora of the female user for preventing fluid bypassing said central portion.

8. The absorbent feminine hygiene article of claim 1 wherein said central portion has a pair of lateral sections each located lateral to the center ridge, said central portion having a maximum thickness defined between said center ridge and a nadir of said lower face of said central portion located on said lower face of said central portion opposite said center ridge of said central portion, the thickness of said central portion tapering gradually thinner from the maximum thickness of said central portion toward each of said sides of said central portion for resisting bending of said lateral sections of said central portion with respect to said center ridge.

* * * * *